(12) United States Patent
Sawalski

(10) Patent No.: US 8,322,525 B2
(45) Date of Patent: Dec. 4, 2012

(54) ANTIBACTERIAL HOLDERS FOR CLEANING IMPLEMENTS

(75) Inventor: Michael M. Sawalski, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 12/913,009

(22) Filed: Oct. 27, 2010

(65) Prior Publication Data
US 2012/0103839 A1  May 3, 2012

(51) Int. Cl.
*B65D 81/24* (2006.01)
(52) U.S. Cl. ........................ 206/207; 206/205; 206/524.1
(58) Field of Classification Search ................. 206/77.1, 206/204, 205, 207, 208, 524.1, 524.6, 524.3; 248/346.11; 220/574; 15/1, 184, 185, 257.01
See application file for complete search history.

(56) References Cited

U.S. PATENT DOCUMENTS

| | | | |
|---|---|---|---|
| 750,833 A | 2/1904 | Eddy | |
| 1,659,644 A | 2/1928 | Vernet | |
| 1,756,713 A | 4/1930 | Vernet | |
| 3,860,536 A * | 1/1975 | Landwerlen et al. | 510/284 |
| 4,214,657 A | 7/1980 | Winston | |
| 4,323,466 A * | 4/1982 | Curry et al. | 510/319 |
| 4,356,203 A * | 10/1982 | Ueno et al. | 426/266 |
| 4,831,681 A * | 5/1989 | Puder | 15/257.05 |
| 5,064,663 A * | 11/1991 | Murray et al. | 426/60 |
| 5,887,769 A | 3/1999 | Kidd | |
| 5,938,162 A | 8/1999 | Honjo | |
| 5,941,379 A * | 8/1999 | Barardo | 206/209 |
| 2004/0191141 A1 | 9/2004 | Margolis | |
| 2006/0172013 A1* | 8/2006 | Hirai | 424/630 |
| 2007/0181448 A1 | 8/2007 | Davis | |
| 2008/0149504 A1* | 6/2008 | Benjamin et al. | 206/223 |
| 2009/0188816 A1* | 7/2009 | Purohit | 206/208 |

FOREIGN PATENT DOCUMENTS
KR   20010088990 A    9/2001
KR   20010088990 A  * 9/2001

OTHER PUBLICATIONS

A one p. Feb. 1, 2010 web site excerpt from DollarDays.com, entitled Wholesale Tilon All Purpose Fiber Antibacterial Sponge.
A two page Feb. 1, 2010 web site excerpt from ehow.com, entitled "How to Clean Sponges With Salt".
A one page Feb. 1, 2010 web site excerpt from wikipedia.org, entitled "Salt-cured meat".
A one page Feb. 1, 2010 web site excerpt from irawoods.com, entitled Lefroy Brooks LB4950 Edwardian Wire Sponge Dish.
PCT/US2011/001817 International Search Report dated Feb. 3, 2012.

* cited by examiner

Primary Examiner — Steven A. Reynolds

(57) ABSTRACT

Holders for automatically treating cleaning implements (e.g. kitchen sponges) with antibacterial chemicals during storage are disclosed. These holders have a solid compressed chemical surface for contacting the cleaning implement between uses. Moisture from the used cleaning implement dissolves a small amount of the chemical (e.g. sodium chloride), thereby causing the chemical to treat the contact surface of the cleaning implement. Merely by placing a sponge or the like on a coaster, or against another holder surface, bacterial growth on the sponge or the like can be inhibited, thereby extending the useful life of such cleaning implements.

7 Claims, 4 Drawing Sheets

ANTIBACTERIAL HOLDERS FOR CLEANING IMPLEMENTS

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

The present invention relates to holders for kitchen sponges, dish rags and other cleaning implements between uses. More particularly it relates to holders that upon contact with the cleaning implements deliver an antibacterial chemical to the cleaning implements.

Kitchen sponges, dish rags, toilet bowl brushes and other cleaning implements are typically wetted and exposed to dirt and germs when used. Many such cleaning implements are capable of being reused. For example, after using a conventional synthetic or natural sponge to wipe a countertop surface one typically rinses out the sponge, squeezes it, and then places it on a dish or the like until the next need for the sponge arises. A dish rag might be used in a similar manner, albeit more often for cleaning dishes rather than countertops.

However, such wetted sponges/towels/rags can develop bacterial growth between uses, thereby creating undesirable odors and an unsightly appearance. Thus, there have been attempts to clean such cleaning implements more thoroughly before storage. Some have tried extended rinsing and squeezing when the primary use is over. However, this takes up an undesirable amount of extra time, and can still not avoid some bacterial growth between uses.

Others have therefore tried to soak the cleaning implement in an antibacterial solution between uses, or at least for a portion of the normal storage time between uses. While this does tend to inhibit bacterial growth on the cleaning implement between usage, it requires the consumer to create and use a bath of antibacterial solution, rather than simply putting away the cleaning implement after the primary use.

Still others have sought to pre-impregnate the cleaning implement with an anti-bacterial chemical. However, this anti-bacterial chemical may limit what surfaces and environments the cleaning implement can be used in/with. Further, extended rinsing when using such implements may degrade the antibacterial protection over time.

Sponges, dish rags and the like are often stored on drip racks between uses. These racks are designed to allow moisture to drip down off and away from the cleaning implements, or at least more readily evaporate there from, to thereby help dry the cleaning implement. However, this still can leave some opportunity for bacterial growth.

There have also been attempts to form soap dish-like objects for storing cleaning implements between uses, where the dish-like object is made from a highly absorbent material. These dishes are designed to draw liquid away from the cleaning implement. See e.g. U.S. Pat. Nos. 750,833, 1,659, 644, 1,756,713 and 5,938,162. However, this still can leave the cleaning implement damp enough to permit undesired bacterial growth. Further, the dish itself can create another surface where bacterial growth may occur.

Hence, a need still exists for improved means of storing damp cleaning implements between uses with reduced incidence of bacterial growth thereon.

BRIEF SUMMARY OF THE INVENTION

The invention provides an antibacterial holder for a cleaning implement. The holder has at least one surface for contacting a moist cleaning implement between uses. For example, the holder can be an open top structure in the form of a dish or coaster. A wet sponge, dish rag, dish towel or similar cleaning implement that normally becomes damp during use can be placed on a top surface of the holder and stored there between uses. The structure of the holder is such that when such a moist cleaning implement is positioned thereon antibacterial chemical from the holder automatically dissolves to some extent and bleeds onto an outer surface of the cleaning implement, thereby inhibiting bacterial growth on that surface.

In preferred forms:

(a) the holder is in the form of a dish or coaster, or in the form of a container having external walls and an internal cavity;

(b) where the holder is in dish or coaster form it may have an upper portion that is formed from a compressed antibacterial chemical such as sodium chloride. Alternatively, the entire holder may be made from that material. Sodium chloride is highly preferred as it not only is an effective antibacterial, it is available at very low cost, and is safe in a food environment. Other antibacterials can also be included such as honey and/or essential oils (e.g. tea tree oil);

(c) the holder may also have a lower tray portion (e.g. made of plastic or ceramic) which prevents the upper portion from contacting the countertop, sink or other supporting surface;

(d) the upper portion may also contain other chemicals such as a fragrance (e.g. pine oil, citrus oil, lime oil), or a surfactant (e.g. Glucopan 425N) to pre-impregnate the cleaning implement for the next use;

(e) the holder may have external walls and an internal cavity that has its walls formed of (or coated with) the antibacterial chemical.

(f) the holder may be in the form of a saddle suitable to mount on a divider of a multi-basin sink.

A particularly preferred form of antibacterial chemistry is to form contacting portions of the holder of sodium chloride mixed with small amounts (less than 3%) of water or other liquid. The material is then preferably compressed/molded under pressure to form the desired shape (e.g. a slab; a dish; a rectangular cup liner).

One such formula would be 90% sodium chloride, 8% sugar and 2% water. Another such formula would be 98% sodium chloride and 2% water. Still another would be 95% sodium chloride and 5% "clean linen" smell fragrance. Yet another would be 90% sodium chloride and 10% Glucopan 425N surfactant.

It will be appreciated that without the consumer needing to take any extra steps besides positioning the cleaning element at a storage location the useful life of a sponge, dish rag or the like can be extended. A consumer need only place the cleaning implement (e.g. on a soap dish-shaped object), and achieve the desired antibacterial function automatically.

If it is desired to treat multiple sides of a toilet bowl brush, sponge or the like simultaneously, that cleaning implement can be wedged into a disinfecting confining container, so that the walls contact multiple sides of the implement. In the storage time that is typical between uses enough salt can transfer to these surfaces to disinfect them all.

With a toilet bowl brush a tapered cylindrical holder can preferably be formed so that between uses the bristles of the brush are forced into better contact with the surrounding salt walls.

The amount of salt transferred to the cleaning implement during any one storage cycle is so small that use of the implement is unlikely to coat surfaces with visible salt residues. In any event, typical kitchen surfaces are not adversely affected by salt solutions, and consumers will often wet and squeeze out such an implement before reuse anyway.

Also, the cost of producing such holders is very low, rendering it practical to use such holders as compared to prematurely throwing away sponges and the like.

The foregoing and other advantages of the present invention will be apparent from the following description. In that description reference is made to the accompanying drawings which form a part thereof, and in which there is shown by way of illustration, and not limitation, preferred embodiments of the invention. Such embodiments do not necessarily represent the full scope of the invention, and reference should therefore be made to the claims herein for interpreting the scope of the invention.

DETAILED DESCRIPTION OF THE PREFERRED EMBODIMENTS

Figure 1:
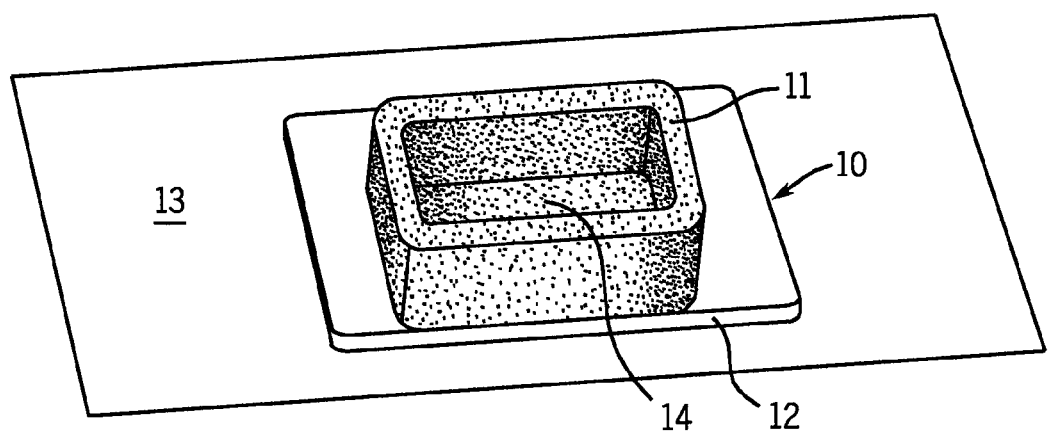
FIG. 1 is a perspective view of a dish form of a holder of the present invention, which has been mounted on a protective surface.

Referring first to FIG. 1, there is shown a cleaning implement holder 10 of the present invention. Its upper layer 11 is made from compressed sodium chloride. Its lower layer 12 is designed to protect the countertop or other surface 13 that the holder is placed on from becoming coated with salt from the holder 10. The lower layer 12 may be formed from plastic, ceramic, glass, or other material. Alternatively, it can be eliminated.

Figure 2:
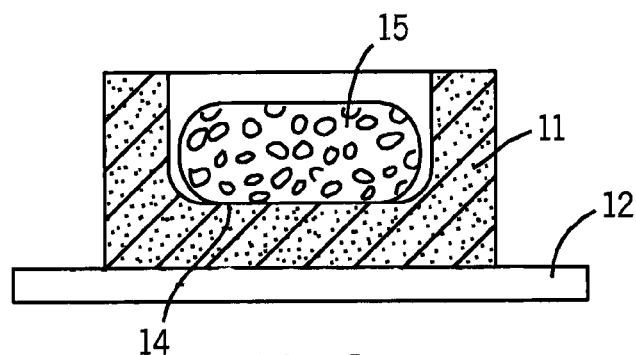
FIG. 2 is a vertical sectional view thereof, once a used sponge has been positioned thereon between uses.

As shown in FIG. 2, a moist, recently used, sponge 15 is positioned on a contacting surface 14 of the upper layer 11, and left there between uses. That contacting surface comprises a solid antibacterial chemical. A wetting agent (e.g. water) is used to help the salt stick together. The amount of wetting agent, the amount of other materials used with the antibacterial material, the amount and time of pressure, and other related parameters can fine tune the amount of antibacterial chemical delivered to the moist cleaning implement from each contact.

Note that the upper layer 11 doesn't simply absorb moisture from the sponge 15. Rather, it is configured and formed so as to slowly dissolve into liquid provided by the cleaning element, and then deliver back that solution of antibacterial chemical.

In one example, to form a contacting layer 290 gm of sodium chloride can have added to it 15 ml of distilled water. This solid mixture can then be compressed using a machined steel tool and 36 ton press. This precursor can be held at pressure for about half a minute and then be removed from the tool. It is then a sufficiently secure solid so as to be transferred to a support tray.

Salt is a particularly preferred disinfectant as it won't damage most household hard surfaces, has a well established effectiveness against a wide range of bacteria, and is generally recognized as safe around food. For certain applications the salt can be supplemented with fragrance or other desired deliverable chemicals. For example, an amount of limonene (orange oil) can be added to the salt.

Figure 3:
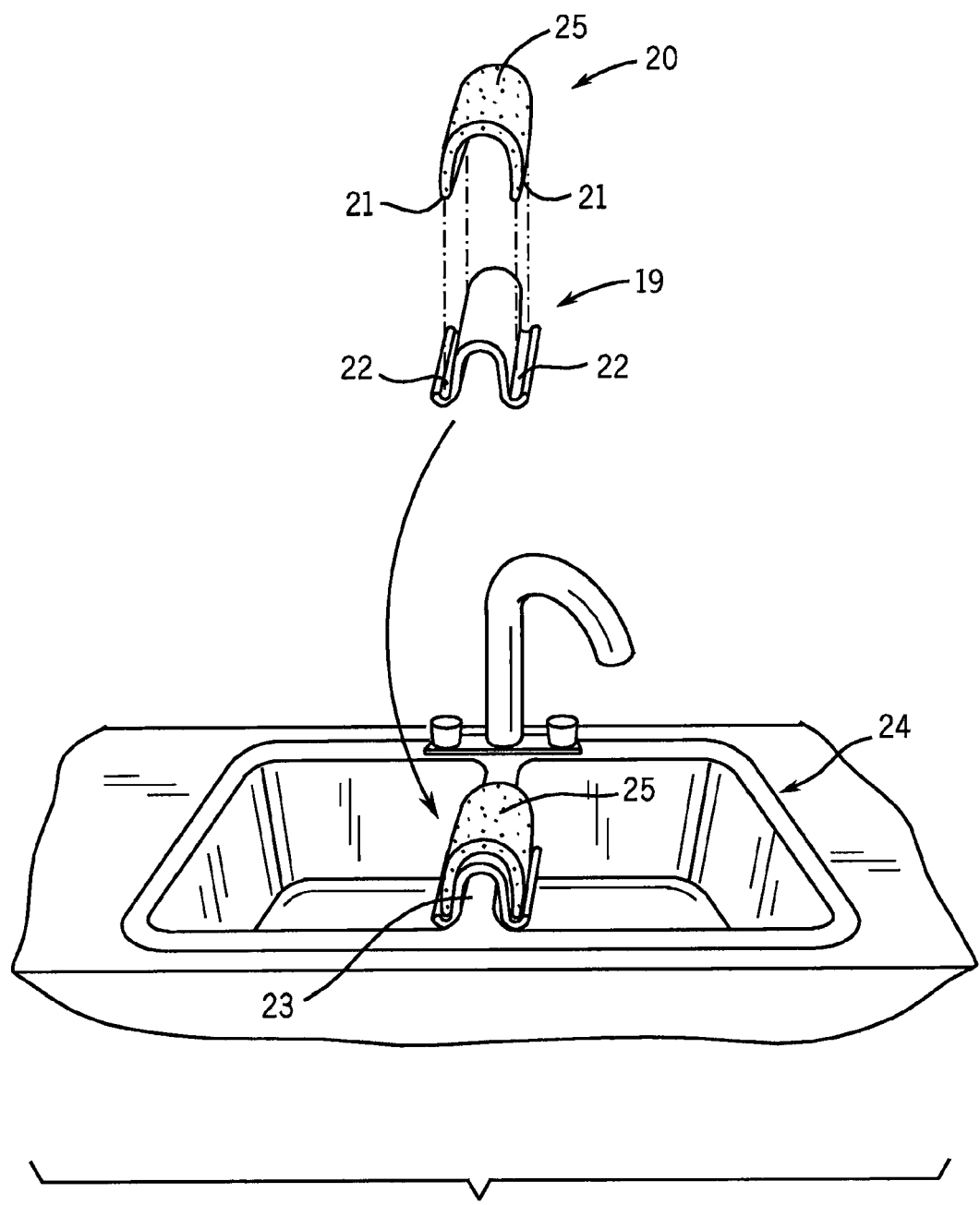
FIG. 3 is a schematic perspective depiction of how a saddle form of the present invention can be pre-assembled and then mounted on a sink divider.

As shown in FIG. 3, the holder can alternatively constitute a plastic saddle 19 on which is placed a saddle-shaped salt refill 20. The lower edges 21 of the refill can rest in recessed pockets 22 along the saddle. The holder can then be mounted over a divider 23 of a conventional sink 24, with a sponge or rag then positionable on surface 25 between uses.

Figure 4:
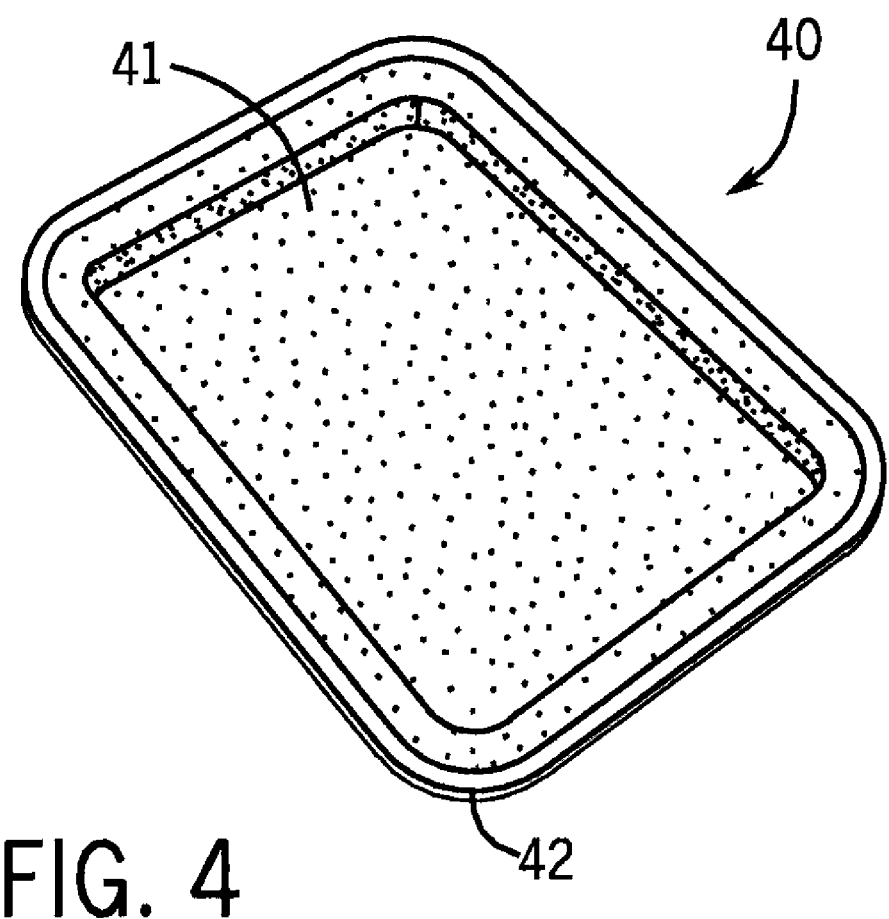
FIG. 4 is a coaster form of a holder of the present invention.

FIG. 4 depicts another form of the invention. Here the holder is coaster form. There is an upper layer 41 made of compressed salt and a protective tray 42 made of plastic. For appearance sake here the layers are ornamentally conformed in shape.

Figure 5:
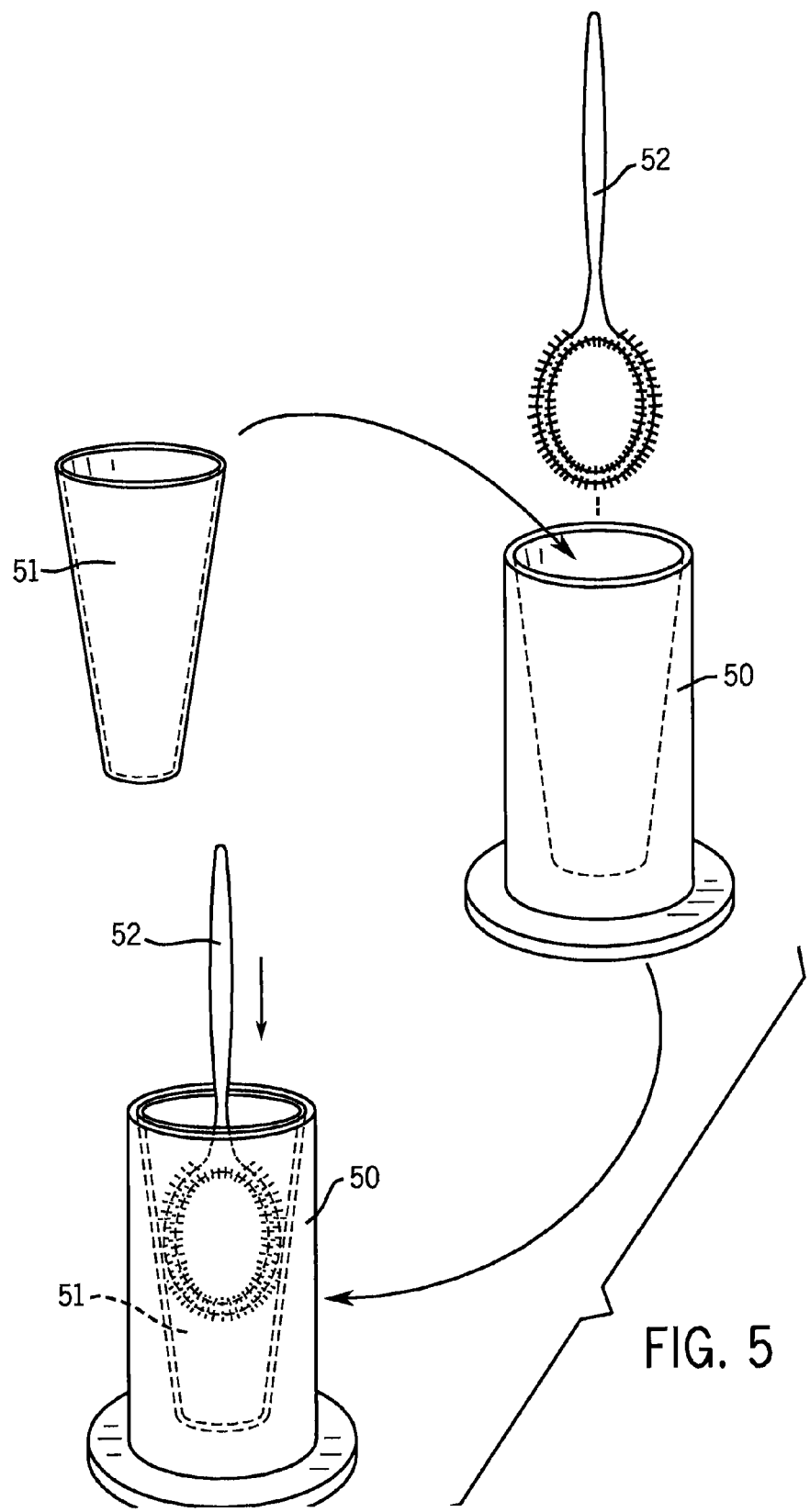
FIG. 5 is a schematic perspective view of how a toilet brush holder form of the present invention can be assembled and used.

FIG. 5 depicts another holder 50 in which is placed a compressed salt cone 51. Then, between uses, a toilet brush 52 is wedged into the cone 51 for storage and treatment. This treats the bottom of the brush, as well as the surrounding sides, simultaneously.

A similar concept could be used to treat multiple sides of a sponge simultaneously. For example, the holder could have a toaster-shaped configuration to accept the sponge in a wedging rectangular pocket.

The concepts of the present invention can therefore be used with cleaning implements of other shapes. In each case the holder will be sized to provide a suitable rest and treating site. Thus, while preferred embodiments of the present invention have been described above, it should be appreciated that the invention could be used in a variety of other embodiments. Such other modifications may be made without departing from the spirit and scope of the invention. Thus, the claims (rather than just the preferred embodiments) should be reviewed in order to understand the full scope of the invention.

INDUSTRIAL APPLICABILITY

Disclosed are improved holders for treating cleaning implements such as sponges with antibacterial chemicals between uses.

What is claimed is:

1. A cleaning implement holder, comprising:
   a holder wall structure that has at least an upper wall portion that has been formed from a solid antibacterial chemical that was compressed to form the upper wall portion;
   a surface along the upper wall portion for contacting a cleaning implement;
   wherein the surface is configured such that upon a moist cleaning implement being placed on the surface at least some of the antibacterial chemical dissolves into moisture of the cleaning implement and transfers from the surface to the cleaning implement to thereby help retard bacterial growth on the cleaning implement.

2. The cleaning implement holder of claim 1, wherein the compressed antibacterial chemical is sodium chloride.

3. The cleaning implement holder of claim 1, wherein the holder is in the form of a dish or coaster and the holder further comprises a lower tray portion.

4. The cleaning implement holder of claim 1, wherein the upper portion further comprises a fragrance.

5. The cleaning implement holder of claim 1, wherein the holder is in the form of a saddle suitable to mount on a divider of a multi-basin sink.

6. The cleaning implement holder of claim 1, wherein the holder is formed at least in part of solid sodium chloride which has been compressed under pressure.

7. The cleaning implement holder of claim 1, wherein the cleaning implement is a sponge.

\* \* \* \* \*